(12) United States Patent
Johns et al.

(10) Patent No.: US 8,343,491 B2
(45) Date of Patent: Jan. 1, 2013

(54) ANTI-HIMF ANTIBODIES TO TREAT LUNG DISEASES

(75) Inventors: Roger A. Johns, Reisterstown, MD (US); Qingning Su, Germantown, MD (US); Hunter Clay Champion, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 104 days.

(21) Appl. No.: 12/518,857

(22) PCT Filed: Dec. 18, 2007

(86) PCT No.: PCT/US2007/087899
§ 371 (c)(1),
(2), (4) Date: Aug. 10, 2009

(87) PCT Pub. No.: WO2008/077022
PCT Pub. Date: Jun. 26, 2008

(65) Prior Publication Data
US 2010/0028355 A1    Feb. 4, 2010

Related U.S. Application Data

(60) Provisional application No. 60/875,504, filed on Dec. 18, 2006.

(51) Int. Cl.
*A61K 39/395*    (2006.01)

(52) U.S. Cl. ............... 424/139.1; 424/141.1; 424/145.1; 530/387.9; 530/388.24

(58) Field of Classification Search ................. None
See application file for complete search history.

(56) References Cited

U.S. PATENT DOCUMENTS

| | | | |
|---|---|---|---|
| 7,109,302 B1 * | 9/2006 | Baker et al. | 530/387.1 |
| 2004/0018980 A1 * | 1/2004 | Gurney et al. | 514/12 |
| 2009/0162375 A1 * | 6/2009 | Blake et al. | 424/158.1 |

FOREIGN PATENT DOCUMENTS

| | | | |
|---|---|---|---|
| WO | WO 99/55868 A2 | | 11/1999 |
| WO | WO 02/38797 A2 | | 5/2002 |
| WO | WO 2004071573 A2 | * | 8/2004 |
| WO | WO 2009042504 A1 | * | 4/2009 |

OTHER PUBLICATIONS

Minkoff et al., J Manag Care Pharm. Jul. 2005:11(6 Suppl A):S1-22.*
Morgan et al., Int J Radiat Oncol Biol Phys. Jan. 15, 1995;31(2):361-9. abstract only.*
Vaillant et al., Monaldi Arch Chest Dis. Apr. 1996;51(2):145-52. abstract only.*
Wong, Fred W.S., "Tyrosine Kinase Inhibitors: A New Approach for Asthma", Biochimica et Biophysica Acta 1697, pp. 53-69, (2004).
WS Fred Wong, "Inhibitors of the Tyrosine Kinase Signaling Cascade for Asthma", Current Opinion in Pharmacology, 2005, vol. 5, pp. 264-271.
Popescu, "Antisense- and RNA Interference-based Therapeutic Strategies in Allergy", Journal of Cellular and Molecular Medicine, vol. 9, No. 4, 2005, pp. 840-853.
International Search Report for PCT/US2007/087899 (WO 2008/077022 A2) Issued Jun. 26, 2008.

* cited by examiner

*Primary Examiner* — Michael Szperka
(74) *Attorney, Agent, or Firm* — Johns Hopkins Technology Transfer

(57) ABSTRACT

Hypoxia induced mitogenic factor (HIMF) is a member of the "found in inflammatory zone" (FIZZ)/resistin family of proteins and has potent mitogenic, angiogenic, and vasoconstrictive effects in the lung vasculature. We use antibodies to HIMF to treat certain diseases including adult respiratory distress syndrome, radiation-induced pulmonary fibrosis, idiopathic pulmonary fibrosis, and emphysema.

1 Claim, 5 Drawing Sheets

ANTI-HIMF ANTIBODIES TO TREAT LUNG DISEASES

This invention was made using funds from the United States Government. Under the terms of grant no. R01HL39706 from the National Institutes of Health, the U.S. Government retains certain rights in the invention.

TECHNICAL FIELD OF THE INVENTION

This invention is related to the area of pulmonary, cardiac, and inflammation disorders. In particular, it relates to methods for treatment of these disorders and screening for therapeutic agents to treat these disorders.

BACKGROUND OF THE INVENTION

Hypoxia-induced mitogenic factor (HIMF), also called "found in inflammatory zone 1" (FIZZ1) or resistin like molecule alpha (RELMα) or resistin, is induced in the lungs of experimental models of hypoxia-induced pulmonary hypertension (1, 2). We have shown that HIMF is expressed in the remodeling of hyperplastic vascular smooth muscle in vivo and can stimulate pulmonary microvascular mitogenesis in vitro. Also, we have demonstrated that HIMF possesses angiogenic and vasoconstrictive properties. In addition, HIMF increases pulmonary artery pressure and pulmonary vascular resistance more potently than endothelin, angiotensin or serotonin (1). Not only was HIMF expression increased in the lung vasculature, it was markedly up-regulated in hypertrophic, hyperplastic bronchial epithelium during allergic pulmonary inflammation in mouse models of acute pulmonary inflammation (3). A recent report has also demonstrated HIMF to be expressed in the lymph nodes (4), with the highest expression in B cells and macrophages.

The FIZZ/resistin gene family has been implicated in a variety of human diseases, but their binding partners/receptors until now had not been identified. Resistin which is one of two human analogs of HIMF, has recently been implicated in human vascular disease related to diabetes and to obesity (5). Resistin is greatly up-regulated in obesity and after insulin treatment, thus providing a potential molecular link between obesity and diabetes. It may function as a regulator of glucose homeostasis and an antagonist to insulin action (6). XCP1/FIZZ2 was found to be a chemotactic factor to myeloid cells from C/EBP-epsilon-null mice and is able to interact directly with alpha-defensin (7). There are three members of the FIZZ/resistin family that are encoded by two different genes in human, and five members of the FIZZ/resistin family that are derived from four genes in mouse. Receptors have not yet been identified for any of these physiologically and pathologically important rodent or human isoforms, leaving our functional understanding of this family of proteins incomplete.

Increasing evidence indicates that bone marrow-derived endothelial progenitor cells (EPCs) or circulating hematopoietic stem cells play an important role in postnatal neovascularization of adult ischemic tissues and injured tissues (8-11). Endogenous stimuli like tissue ischemia and exogenous cytokine therapy mobilize EPCs and thereby contribute to the neovascularization of ischemic and injured tissues (12). A number of chemokines have been reported to act as chemotactic and angiostatic molecules in inducing endothelial cell migration and regulating angiogenesis (13,14). In inflammatory diseases, angiogenesis and inflammatory disorders are two inter-related processes regulated by chemokines. XCP1, another member of FIZZ/resistin family sharing 70% identity in amino acid sequence with HIMF, has been reported to be a secreted protein that is chemotactic to myeloid cells, and may also have a role in cell migration, activation, and chemotaxis (7). Although EPCs are rare in the circulation, they can be mobilized into circulation from bone marrow by vascular trauma or systemic administration of cytokines (12, 13, 15, 16). Multipotent adult progenitor cells (MAPC) derived from postnatal human bone marrow were demonstrated to be progenitors for angioblasts and to undergo a differentiation process from CD34(−), VE-cadherin(−) cells to CD34(+), VE-cadherin(+) cells after culture in the presence of VEGF. These cells subsequently differentiate into morphologically and functionally mature endothelial cells that contribute to neoangiogenesis in vivo during tumor angiogenesis and wound healing (15,17).

The role of HIMF in hypoxic tissue and how HIMF exerts its angiogenic and vasoconstrictive properties remain unclear. The current work defines a targeted molecular binding partner of HIMF and investigates whether HIMF functions as a chemotactic molecule for recruiting bone-marrow derived cells to hypoxic or ischemic tissue like its homolog XCP1. To determine HIMF's major binding partner(s) we used GST-pull-down and mass spectrometry techniques. We isolated a HIMF-binding molecule, BTK, a molecule known to be crucial in regulation of B-cell maturation and involved in cell migration. BTK stimulates B cell differentiation in bone marrow, and mutations in BTK are responsible for X-linked agammaglobulinemia (XLA) in humans and X-linked immunodeficiency (xid) in mice (18, 19). Since HIMF expression is induced in hypoxic tissue, and bone marrow derived EPCs are preferentially recruited to the site of ischemic tissue, we investigated whether HIMF is a chemotactic molecule for bone marrow cells.

There is a continuing need in the art to identify important targets for treating pulmonary, cardiac, and inflammatory diseases.

SUMMARY OF THE INVENTION

According to one embodiment of the invention a method of treating a patient with inflammatory lung disease is provided. An agent is administered to the patient. The agent is selected from the group consisting of: an antibody which specifically binds to HIMF (SEQ ID NO: 1 or 2); an antibody which specifically binds to BTK (SEQ ID NO: 3); an RNAi which is complementary to an mRNA of HIMF (SEQ ID NO:4 or 5); and an RNAi which is complementary to an mRNA of BTK (SEQ ID NO: 6). Expression of HIMF or BTK is thereby suppressed or binding of HIMF to BTK is inhibited.

Another aspect of the invention is a method of screening for a candidate drug for treating inflammation. Binding of HIMF (SEQ ID NO: 1 or 2) with BTK (SEQ ID NO: 3) is determined in the presence and absence of a test substance. A test substance that reduces binding of HIMF to BTK is identified as a candidate drug for treating inflammation.

According to another embodiment of the invention a method of treating a patient with cholesterol levels which are higher than a recommended normal range is provided. An agent is administered to the patient. The agent is selected from the group consisting of: an antibody which specifically binds to HIMF (SEQ ID NO: 1 or 2); an antibody which specifically binds to BTK (SEQ ID NO: 3); an RNAi which is complementary to an mRNA of HIMF (SEQ ID NO:4 or 5); and an RNAi which is complementary to an mRNA of BTK (SEQ ID NO: 6). Expression of HIMF or BTK is thereby suppressed or binding of HIMF to BTK is inhibited.

According to one embodiment of the invention a method of treating person with inflammation, dementia, cancer, nuclear cataract, atherosclerosis, sarcoidosis, or pulmonary hypertension is provided. An agent is administered to the person. The agent is selected from the group consisting of: an antibody which specifically binds to HIMF (SEQ ID NO: 1 or 2); an antibody which specifically binds to BTK (SEQ ID NO: 3); an RNAi which is complementary to an mRNA of HIMF (SEQ ID NO:4 or 5); and an RNAi which is complementary to an mRNA of BTK (SEQ ID NO: 6). Expression of HIMF or BTK is thereby suppressed or binding of HIMF to BTK is thereby inhibited. Similarly, a statin drug can be used to treat these conditions.

A further aspect of the invention provides a method to diagnose severity of asthma. The amount of HIMF (SEQ ID NO: 1 or 2) in a nasal swab or lung washing of a subject is determined. The amount of HIMF correlates with severity of asthma.

According to still another embodiment of the invention a method is provided for treating a patient with cardiac hypertrophy, ischemia, or heart failure. An agent is administered to the patient. The agent is selected from the group consisting of: an antibody which specifically binds to BTK (SEQ ID NO: 3); and an RNAi which is complementary to an mRNA of BTK (SEQ ID NO: 6). Expression of BTK is thereby suppressed or binding of HIMF to BTK is thereby inhibited.

Yet another embodiment of the invention is a method of screening for a candidate drug for treating inflammation. Bone marrow cells are stimulated with HIMF (SEQ ID NO: 1 or 2) in the presence and absence of a test substance. Phosphorylation of BTK (SEQ ID NO: 6) in the bone marrow cells is determined. A test substance that reduces phosphorylation of BTK in response to HIMF stimulation is identified as a candidate drug for treating inflammation.

Still another aspect of the invention is a method to diagnose pulmonary hypertension. The amount of HIMF (SEQ ID NO: 1 or 2) in a serum sample of a subject is determined. A serum sample that has an amount of HIMF greater than an amount of HIMF in normal, non-pulmonary hypertensive controls is identified as belonging to a subject with pulmonary hypertension.

These and other embodiments which will be apparent to those of skill in the art upon reading the specification provide the art with

DETAILED DESCRIPTION OF THE INVENTION

Figure 1A:
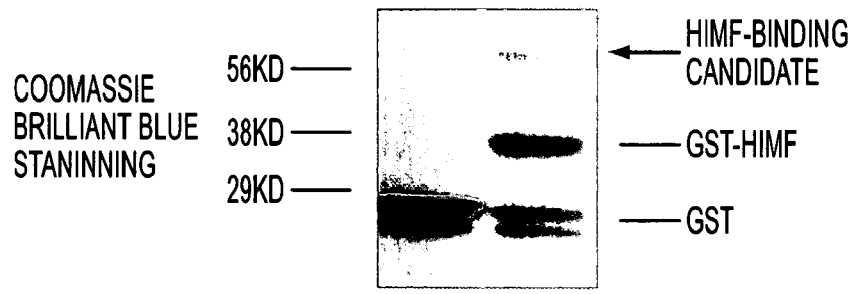
FIGS. 1A-1B. BTK is a HIMF-binding molecule. GST-HIMF fusion protein and GST were incubated with glutathione-sepharose beads and then incubated with bone marrow cell lysate respectively in TBST buffer at 4° C. for three hours. The beads were washed five times by TBST and loading buffer was added to the samples. After electrophoresis, the gel was stained by Coomassie Blue. The arrow shows a HIMF-binding candidate protein (FIG. 1A). GST-HIMF and GST were first bonded to glutathione sepharose and then incubated with the lysate of bone marrow cells (left) or homogenate of ischemic tissue (right) at 4° C. for three hours and then washed by TBST solution three times. After SDS-PAGE and transfer to membrane, the samples were detected by anti-BTK and anti-GST antibodies (FIG. 1B).

The inventors have discovered a functional binding partner of HIMF which is BTK. Inhibition of binding of either partner to the other prevents the functional and often pathological consequences of binding. Antibodies specifically binding to either HIMF or BTK can be used. Antibodies which prevent the binding of the antigen to its partner can be used to provide a therapeutic effect. Similarly, interfering RNA (RNAi) which suppresses expression of the HIMF or BTK product can be used.

HIMF is used to collectively denote either of the two human protein forms known as resistin and relm-beta. These are encoded by genes denoted as RETN and RETNLB. Exemplary human sequences from the public databases are represented as SEQ ID NO: 1 (resistin), SEQ ID NO: 2 (relm-beta), SEQ ID NO: 3 (Bruton agammaglobulinemia tyrosine kinase), SEQ ID NO: 4 (RETN), SEQ ID NO: 5 (RETNLB), and SEQ ID NO: 6 (BTK) in the sequence listing. Minor variations occur in any human population of proteins and genes which do not change function or the vast majority of the structure. Such minor variations, known as polymorphisms, are encompassed. Typically these are single nucleotide changes and/or single amino acid changes.

Diseases which can be treated using the HIMF/BTK antibodies, binding inhibitors, and interfering RNAs include any inflammatory lung disease, including but not limited to Scleroderma, idiopathic pulmonary fibrosis, sarcoidosis, asthma, emphysema, adult respiratory distress syndrome, radiation-induced pulmonary inflammation or fibrosis, chemotherapy-induced pulmonary inflammation or fibrosis, and chronic obstructive pulmonary disease. Other types of inflammation including dementia, cancer, nuclear cataracts, and pulmonary hypertension can also be treated. In addition, heart conditions including but not limited to cardiac hypertrophy, ischemia, atherosclerosis, and heart failure are also amenable to such treatments. In addition, since statin drugs have been found to decrease amount of HIMF in lungs, statin drugs can be used to treat any of these conditions and diseases as well, particularly the lung diseases.

Statin drugs are inhibitors of HMG-CoA, i.e., hydroxy-3-methylglutaryl coenzyme A. reductase. These include, but are not limited to atorvastatin, cerivastatin, fluvastatin, lovastatin, mevastatin, pitavastatin, pravastatin, rosuvastatin, simvastatin. These can also be used in combinations with, for example, ezetimibe, niacin, and/or amlodipine besylate.

One of ordinary skill in the art can readily generate antibodies which specifically bind to the HIMF or BTK proteins. Such antibodies can be monoclonal or polyclonal. They can be chimeric, humanized, or totally human. Any functional fragment or derivative of an antibody can be used including Fab, Fab', Fab2, Fab'2, and single chain variable regions. So long as the fragment or derivative retains specificity of binding for the protein it can be used. Antibodies can be tested for specificity of binding by (a) comparing binding to appropriate antigen, to (b) binding to irrelevant antigen or antigen mixture, under a given set of conditions. If the antibody binds to the appropriate antigen at least 2, 5, 7, and preferably 10 times more than to irrelevant antigen or antigen mixture then it is considered to be specific. Moreover, the ability of such antibodies or antibody fragments to inhibit the binding of HIMF to BTK can be readily and routinely tested.

Techniques for making such partially to fully human antibodies are known in the art and any such techniques can be used. According to one particularly preferred embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. See for example, Nina D. Russel, Jose R. F. Corvalan, Michael L. Gallo, C. Geoffrey Davis, Liise-Anne Pirofski. Production of Protective Human Antipneumococcal Antibodies by Transgenic Mice with Human Immunoglobulin Loci *Infection and Immunity* April 2000, p. 1820-1826.

Antibodies can also be made using phage display techniques. Such techniques can be used to isolate an initial antibody or to generate variants with altered specificity or avidity characteristics. Single chain Fv can also be used as is convenient. They can be made from vaccinated transgenic mice, if desired. Antibodies can be produced in cell culture, in phage, or in various animals, including but not limited to cows, rabbits, goats, mice, rats, hamsters, guinea pigs, sheep, dogs, cats, monkeys, chimpanzees, apes.

Antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Those of skill in the art will readily understand and be able to make such antibody derivatives, as they are well known in the art. The antibodies may be therapeutic on their own, or they may be used to deliver therapeutic agents to particular locations in the body. The antibodies can be administered to individuals in need thereof as a form of passive immunization.

RNA interference constructs or siRNA duplex RNA molecules can be used to interfere with expression of HIMF or BTK. Typically at least 15, 17, 19, or 21 nucleotides of the complement of HIMF or BTK mRNA sequence are sufficient for an antisense molecule. Typically at least 19, 21, 22, or 23 nucleotides of HIMF or BTK are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired HIMF or BTK sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, *Nature* 418: 244-251; Bernstein E et al., 2002, The rest is silence. *RNA* 7: 1509-1521; Hutvagner G et al., RNAi: Nature abhors a double-strand. *Curr. Opin. Genetics & Development* 12: 225-232; Brummelkamp, 2002, A system for stable expression of short interfering RNAs in mammalian cells. *Science* 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052.

RNA interference molecules can be delivered in vitro to cells or in vivo, e.g., to tumors, eyes, lungs, bronchia, heart, or retina of a mammal. Typical delivery means known in the art can be used. For example, delivery to a tumor can be accomplished by intratumoral injections. Delivery to lung can be accomplished by instillation. Other modes of delivery can be used without limitation, including: intravenous, intramuscular, intraperitoneal, intraarterial, local delivery during surgery, endoscopic, subcutaneous, and per os. In a mouse model, the antisense or RNA interference can be adminstered to a tumor cell in vitro, and the tumor cell can be subsequently administered to a mouse. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

Binding assays according to the invention may be any known in the art. These include in vitro binding of purified proteins, pull-down assays, co-immunoprecipitation assays, in vivo fusion protein assays. Any such assay in which the HIMF and the BTK detectably bind can be used as an assay for screening for candidate drugs and their effect on binding. Candidate drugs can be subsequently tested in animal models and in clinical trials to confirm efficacy and determine safety.

Test substances for drug screening can be any natural or synthetic product, whether a single molecular entity or a mixture of molecular entities. Libraries of compounds can be screened. Natural product extracts can be screened. Products with known or unknown biological functions or drug activity can be screened. Test substances can be small chemical entities, or biological macromolecules, such as proteins, peptides, nucleic acids, carbohydrates, lectins, etc.

Cholesterol lowering effects of inhibition of the HIMF/BTK binding and or expression can be used to treat patients in need thereof. These can be used as substitutes or adjuncts to statin therapy. The normal range of cholesterol is defined in particular populations and may change over time. Persons outside of the determined normal range, adjudged to be in need of cholesterol-lowering therapy, may be treated.

The level of HIMF has been found to correlate with the severity of asthma symptoms. Thus assaying for HIMF and determining the amount of HIMF can be used as a way to characterize, stratify, and plan treatment for asthma patients. Nasal swabs and lung washings are suitable to comprise samples for such assays. Amount of HIMF in such samples can be assayed in the same patient over time to see progression or remission of disease. Alternatively, data from populations of asthma patients stratified on the basis of other symptoms can be used to provide a standard curve for amounts of HIMF in the nasal swabs or lung washings. Similarly the levels of HIMF in serum can be used as a biomarker of pulmonary hypertension, whether idiopathic or related to Scleroderma. Elevated levels compared to control subjects or populations of normal controls subjects who do not have pulmonary hypertension or scleroderma can be used as a reference. Elevated levels are any which are statistically above normal controls; this may be at least 50% greater, at least 75% greater, at least 100% greater, at least 150% greater, at least 200% greater, at least 250% greater, or more. Assays for HIMF can be, for example, immunological, such as by ELISA or western blot. Other means for readily identifying and quantifying HIMF can be used, as are convenient. These include binding assays to BTK.

BTK autophosphorylates in response to HIMF stimulation, at least in bone marrow cells. This biological response can be used as an assay to screen for test substances which reduce, inhibit, or prevent such HIMF-stimulated autophosphorylation. Candidate drugs can be subsequently tested in animal models and in clinical trials to confirm efficacy and determine safety.

The HIMF/FIZZ/resistin family of proteins have been implicated in pulmonary vascular remodeling in rodents and in human vascular disease associated with obesity, diabetes and atherogenesis (1,25,26). Little is known of the mechanisms of action of this family of proteins in vascular disease, and in particular, no receptor or functional binding partner had been identified. Using HIMF in pull-down assays with protein isolated from mouse bone marrow followed by mass spectrometry, we have identified Bruton's Tyrosine Kinase (BTK) as an important functional binding partner of HIMF. Using in vitro (cell migraton assay) and in vivo (hindlimb ischemia model), we have demonstrated HIMF leads to inflammatory and EPC chemotaxis, which is mediated through activation of BTK Mice deficient in the Src family kinases are unable to develop an angiogenic response to chemokines because their neutrophils are unable to release VEGF-A, indicating that soluble tyrosine kinases are important factors in angiogenesis (13). As a member of the Src family of kinases, BTK has been known to be crucial in the regulation of B-cell maturation, and defects in BTK lead to X-linked agammaglobulinemia in humans and X-linked immunodeficiency defect in mice. VEGF receptor 2 (VEGFR-2/Flk1) is the key mediator of VEGF action in endothelial cells. Transcriptional regulation of the VEGFR-2 can be mediated by transcription factors TFII-I/BAP-135 and NF-κB (27). Interestingly NF-κB is an important down-stream mediator for the BTK signaling pathway (28). TFII-I/BAP-135 is also a BTK-associated protein and a substrate of BTK (27, 29). XID mice show increased severity of inflammatory diseases. The bone marrow of XID mice shows a reduction in the numbers of both monocytic and granulocytic lineages, extending to the earliest progenitor populations (19). As a result, the activation of BTK upon stimulation of HIMF may play a significant role in the recruitment of inflammatory cells, mediating the VEGF and chemokine release and regulation of the development of the myeloid lineages (19, 30), and VEGFR-2 expression in endothelial cells.

The BTK family of kinases plays diverse roles in various cellular processes including stimulation of cell growth, differentiation, apoptosis, cytoskeletal reorganization, and cell motility. The mutation of BTK resulting in immunodeficiency diseases further demonstrates the physiological importance of this kinase. In the regulation of differentiation of bone marrow hematopoietic cells into B cells, the BTK pathway is essential. Other members of the BTK family of kinases have been shown to be involved in the signaling pathway of integrins that are key molecules regulating the actin cytoskeleton and cell mobility (31).

Figure 7A:
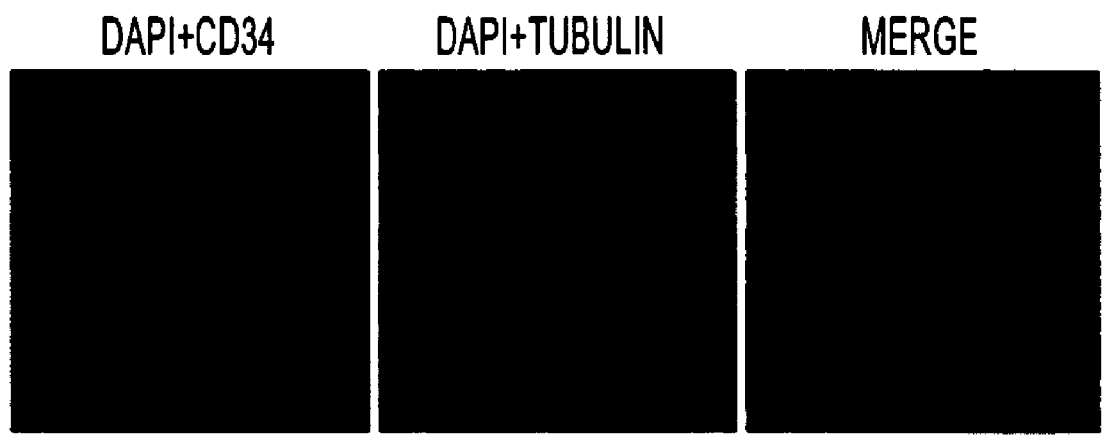
FIGS. 7A-7B. HIMF stimulated angiogenesis in hypoxic tissues. Mouse hind limb ischemia model was established and agarose gel containing 100 nM BSA or 100 nM HIMF (gels were cut into 2×5×8 mm pieces) were buried subcutaneously at the sites of ischemia. Two weeks later, the ischemic tissues were collected for immunocytochemistry. The tissue treated by HIMF (FIG. 7B) was shown increasing in CD34 positive cells comparing to that of BSA treated tissue (FIG. 7A).
Figure 7B:
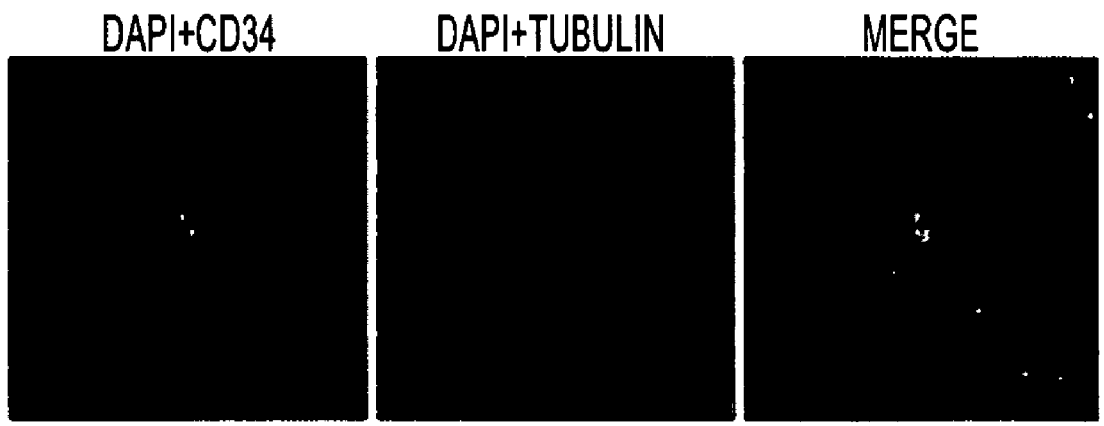

Recent advances in the study of bone marrow-derived endothelial progenitor cells have shown that these cells are involved in neovascularization during ischemic conditions (32). Growth factors and chemotactic molecules released from hypoxic tissues mobilize EPCs from the bone marrow to the hypoxic tissues, which are then thought to form functional vessels with blood flow (33). We have shown that HIMF is one of these molecules that is released from hypoxic tissues and may function as a chemotactic molecule recruiting leukocytes/EPCs to the ischemic area (FIG. 7A-7B).

Using bone marrow cells as the source for seeking binding partners in our study, we demonstrated that BTK is a HIMF binding molecule by mass spectroscopy. As an inflammatory marker (6), HIMF may likely be involved in the regulation of the immune system in response to inflammatory stimulation. A large number of studies have shown that leukocytes act to promote angiogenesis in inflammatory tissues by delivering VEGF to the target sites, where vascular remodeling is important for tissue regeneration. The activation of BTK will induce the differentiation and migration of bone marrow-derived leukocytes or EPCs that may be involved in the inflammatory reaction and neovascularization in hypoxic tissues. Our finding of BTK as a HIMF binding molecule suggests that HIMF-BTK interaction may mediate tissue recovery processes through stimulating the differentiation of EPCs that are involved in angiogenesis and recruiting leukocyte/EPCs to the targeted site. HIMF acting as a chemotactic molecule, like its homolog mXCP1, stimulated migration of bone marrow derived cells to targeted tissue in response to tissue inflammation or hypoxia.

Figures 2A, 2B, 2C:
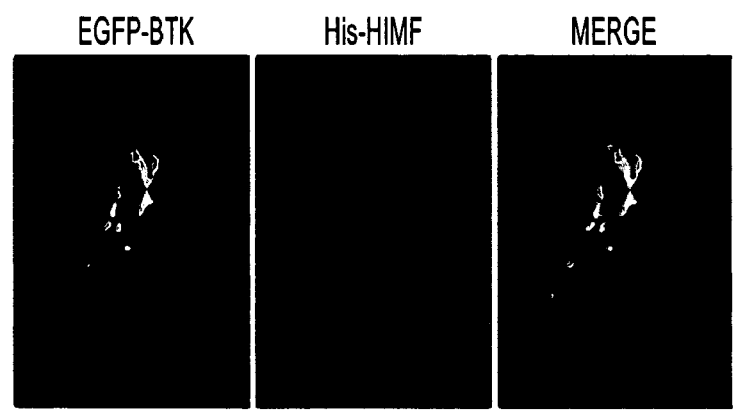
FIG. 2. Co-localization between BTK and HIMF. EGFP-BTK and His-HIMF plasmids were co-transfected into bone marrow cells. The cells were fixed by pre-cooled methanol and stained by anti-his monoclonal antibody and rhodamine-labeled donkey anti-mouse IgG second antibody. EGFP-BTK and his-HIMF co-localized very well in transfected cells.
Figure 3A:
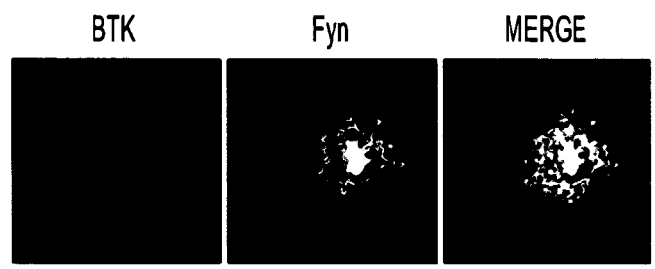
FIGS. 3A-3B. BTK redistribution in response to the stimulation of HIMF. Primary cultured bone marrow. Bone marrow cells were cultured on cover glass and then treated with 50 nM BSA (FIG. 3A) or HIMF (FIG. 3B) for five minutes. Cells were fixed by pre-cooled methanol before indirect immunofluorescence. BTK or FYN, a binding partner for BTK, was redistributed in bone marrow cells after the treatment of HIMF.
Figure 3B:
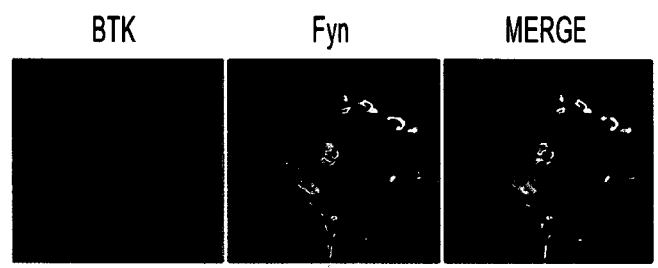
Figure 4A:
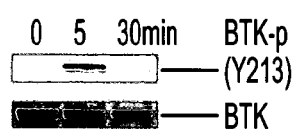
FIGS. 4A-4C. BTK self-phosphorylation in response to the treatment of HIMF. Three plates of primary cultured bone marrow cells that were passed from the same plate of cells were cultured to confluence and then treated with HIMF (5 minutes and 30 minutes), or without HIMF. The cell lysates were used for the Western blot. The membrane was first probed by anti-BTK phosphorylation (Y223) antibody and then was probed by anti-BTK antibody after stripping (FIG. 4A). Five plates of primary cultured bone marrow cells that were passed from same plates of cells were cultured to confluence and then treated with HIMF (2.5, 5, 10 and 20 minutes respectively) or without HIMF. The cell lysates were used for the Western blot. The membrane was first detected by anti-BTK phosphorylation (Y223) antibody and then by anti-tubulin antibody (FIG. 4B). The same samples were used for the detection of fyn phosphorylation (FIG. 4C). Phosphorylation of Y416 upregulates enzyme activity. Phosphorylation of Y528 negatively regulates enzyme activity.
Figure 4B:
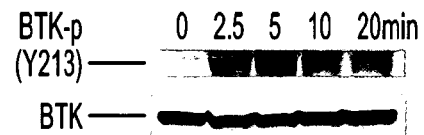
Figure 4C:
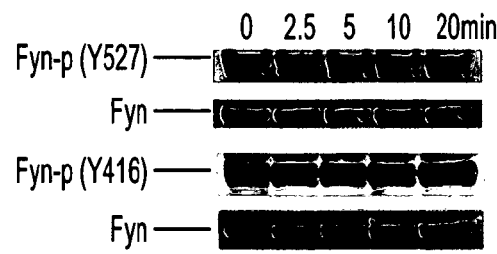

HIMF was up-regulated in both inflammatory and hypoxic tissues and stimulated the phosphorylation of AKT, a kinase with a plextrin homology (PH) domain, in cultured cells (3). Interestingly, BTK is also a PH domain containing molecule. HIMF can also stimulate the self-phosphorylation of BTK in bone marrow cells (FIG. 4A-4C), indicating that BTK is a HIMF-targeted molecule that is activated in response to the stimulation of hypoxia or inflammatory reactions. Fyn, another soluble tyrosine kinase of Src family members, was not changed in activity by the stimulation of HIMF, although Fyn was reported as a BTK-binding protein and shared common distribution with BTK in cells (FIG. 3A-3B). Consequently BTK is a specifically targeted molecule for HIMF. Cells co-transfected with GFP-BTK and His-HIMF plasmids also showed a clear co-localization of BTK and HIMF (FIG. 2).

When bone marrow cells were treated with HIMF, BTK was recruited to the leading edge of the cells (FIG. 3A-3B). This result further indicated that HIMF may stimulate the migration of bone marrow cells. By using a transwell migration assay, we found that HIMF markedly promoted bone marrow cell migration. These migrating bone marrow cells were demonstrated as leukocytes by immunocytochemistry using CD45 antibody (FIG. 6A-6D). The chemotactic characteristic of HIMF was shown to be dependent on the activation of BTK because the BTK inhibitor can totally inhibit the chemokine-like function of HIMF in bone marrow cell migration assay. Hence, HIMF stimulates the migration of bone marrow cells through the activation of BTK and is a chemotactic factor for bone marrow derived leukocytes/EPCs. The recruitment of these cells may contribute to the neovascularization in hypoxic tissues.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Methods and Materials

Constructs and reagents. Flag-tagged HIMF was prepared as described previously (3). GST-HIMF vector was constructed by inserting the coding sequence of mouse HIMF (digested from TA vector with EcoRI and XhoI) into pGEX-5X-1 with the sites of EcoRI and XhoI.

Antibodies and inhibitor. Anti-β tubulin and actin monoclonal antibodies, anti-CD45 rat polyclonal antibody, and anti-Fyn rabbit polyclonal antibody were purchased from Sigma. Anti-BTK monoclonal antibody, anti-BTK phosphorylation (Tyr223), and phospho-Src family (Tyr416) polyclonal antibodies were purchased from Cell Signaling Technology, Inc. Anti-Fyn (pY528) phospho-specific antibody was purchased from BD Transduction Laboratories. Anti-his monoclonal antibody and anti-GST monoclonal antibody were purchased from Novagen. FITC and rhodamine-labeled secondary antibodies were purchased from Jackson ImmunoResearch. BTK inhibitor LFM-A 13 was purchased from Calbiochem.

Cell culture and transfections. COS-7 cells or mouse bone marrow cells were maintained in Dulbecco's modified Eagle's high glucose medium (GIBCO) containing 10% fetal bovine serum at 37° C. and 5% $CO_2$. Cells were transfected with plasmids, as mentioned, using LipofectAMINE 2000 reagent (Invitrogen) according to the manufacturer's protocols. The transfected cells were then fixed in pre-cooled methanol for immunocytochemistry after 24 hours.

GST and GST-HIMF fusion protein expression. BL21 cells harboring GST or GST-HIMF constructs were grown overnight in a 50 ml tube with LB medium containing 50 μg/ml ampicillin and then transferred to a 500 ml flask growing until the OD was 0.6 at 600 nm. The cultures were then induced with isopropyl-β-D-thiogalactopyranoside (IPTG) for an additional 4 hours. Cell lysates were prepared in TBST buffer (50 mM Tris, pH 7.5, 150 mM NaCl, 5 mM EDTA, 1% Triton X-100, 10 μg/ml leupeptin, 10 μg/ml aprotinin, and 1 mM phenylmethylsulfonyl fluoride).

GST pull-down assay. Bone marrow cells were cultured in ten 150×25 mm plates until confluence and collected for lysate using TBST buffer. Lysate from ten plates of bone marrow cells was used for HIMF-binding partner screening assay. Hypoxia tissue homogenate was prepared as described above. BL21 bacterial lysates for GST and GST-HIMF were first incubated with glutathione agarose in 0.1% TBST buffer for three hours and then washed three times by 0.1% TBST buffer. The GST and GST-HIMF binding glutathione agaroses were incubated with bone marrow cell lysate or hypoxia tissue homogenate for three hours and then washed 3-5 times before SDS-PAGE.

Protein phosphorylation assays. Bone marrow cells were cultured in 100×20 mm culture plates and treated with 50 nm BSA or HIMF for different time serials and washed quickly by PBS and lysed in TBST buffer containing 1 mM sodium vanadate. The samples were incubated on ice for 20 min, mixed several times during the incubation, and then centrifuged. The supernatants of the samples were quantified for protein concentration and subjected to electrophoresis on a 4-15% SDS-polyacrylamide gel (Bio-Rad). Anti-BTK phosphorylation (Y-223) polyclonal antibody, anti-BTK, and anti-tubulin monoclonal antibody were used for immunoblotting.

Mouse bone marrow-derived mesenchymal stem cell (MSC) preparation and culture. Six C57BL/6 mice (7 weeks old) were anesthetized with intramuscular injection of 1 mg ketamine plus 0.5 mg xylazine/per animal. Tibiae and femurs were isolated using sterile techniques. The mouse bone marrow cells were prepared by flushing the tibiae and femurs with serum-free DMEM (low glucose, supplemented with 1× Penicillin-Streptomycin and 1 mM EDTA) using 25G needles. Pooled marrow from three animals was first dispersed by gentle pipeting, and then separated by gradient centrifugation with lymphocyte separation liquid (Sigma, density: 1.083 g/ml) as follows: 6 ml of the medium containing the marrow cells was layered on top of 3 ml of separation liquid and centrifuged at room temperature at 2800 rpm for 20 min. The mononuclear cells in the middle layer were collected and then washed with serum-free DMEM three times by centrifugation, first at 2000 rpm for 15 min, then two times at 700 rpm for 10 min. The cells collected after the last wash ($2-3 \times 10^8$) were resuspended in 10 ml DMEM supplemented with 10% FBS and 1× penicillin/streptomycin, and then cultured at 37° C. with 5% $CO_2$ in one 10-cm culture dish (uncoated plastic). Three days later, non-adherent cells were removed by changing medium and the adherent cells were grown for about 2 weeks.

Mouse hindlimb ischemic model. Animals were subjected to left femoral artery ligation and excision to create unilateral hind limb ischemia. For each animal, 25 mg/kg ketamine plus 10 mg/kg xylazine was injected subcutaneously. Skin incisions were performed at the middle portion of the left hind limb overlying the femoral artery. The femoral artery was gently isolated. First the proximal portion and then the distal portion of the femoral artery were ligated, and then other arterial branches as well as veins were dissected free and excised. The overlying skin was closed using two surgical staples. Tissue in the hypoxia area was removed and homogenized in TBST buffer two weeks after the operation.

Cell migration assay. Bone marrow cells were detached with trypsin-EDTA, washed in serum-free medium, and then counted and adjusted to $10^6$ cells/ml. 500 µl of the cell suspension was placed in the Transwell membranes and allowed to migrate to the underside for 6 hours or overnight at 37° C. in the presence of 50 nM BSA, HIMF, or HIMF plus 25 µM of the BTK inhibitor, LFM-A13. The cells were fixed in pre-cooled methanol and stained with Coomassie Blue solution for ten minutes. The cells on the top chamber were removed with a cotton swab, and the cells migrating to the underside of the filter were visualized and photographed using a Nikon Eclipse microscope.

Immunofluorescence microscopy. Bone marrow or COS-7 cells were cultured on coverslips in DMEM containing 10% FBS and fixed in pre-cooled methanol for 5 minutes. The cells were then permeabilized with 0.2% Triton X-100 in PBS and blocked with 0.5% bovine serum albumin in PBS followed by incubation with the indicated antibodies. FITC-donkey anti-rabbit IgG and Rhodamine-donkey anti-mouse IgG were used as second antibodies. For transfection experiments, cells were cultured overnight and transfected with indicated constructs in serum-free medium for four hours and changed into DMEM containing 10% FBS overnight. Cells were fixed and stained as above. A 510 confocal microscope was used for the imaging.

EXAMPLE 2

Figure 1B:
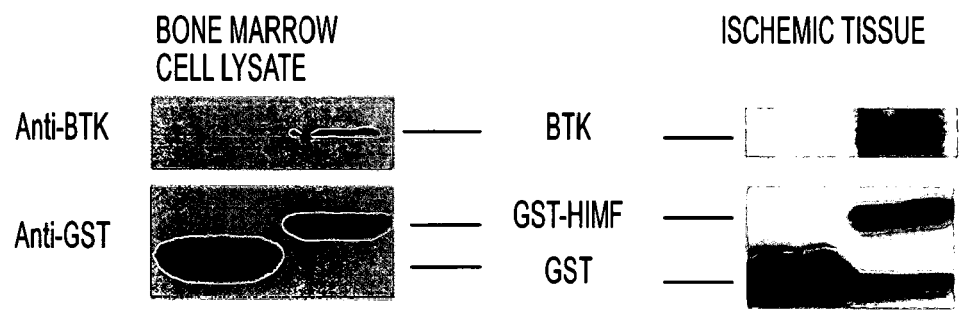

BTK was pulled down by GST-HIMF. To search for HIMF binding partners, we first prepared bacterial lysate for GST and GST-HIMF proteins and then conducted bone marrow cell culture for protein lysates. Glutathione sepharose-bonded GST-HIMF and GST proteins were then used to pull-down the candidate protein from bone marrow cell lysate. As shown in FIG. 1A-1B, GST-HIMF pulled down a protein of approximately 70 kd. The candidate band was cut from the gel and sent for mass spectrometry, where a protein corresponding to BTK, known to be involved in B cell maturation, was identified.

To confirm our finding, we conducted two other binding experiments. First, bone marrow lysate and bacterial lysates of GST and GST-HIMF were used in pull-down assays. BTK antibody was used for detection after the pull-down samples were run on SDS-PAGE and transferred to the PC membrane. As indicated in FIG. 2A, GST-HIMF pulled down BTK from bone marrow cell lysate but GST did not.

To confirm HIMF interaction with BTK in vivo and to assess its role in ischemia and angiogenesis, we employed the established mouse ischemic hindlimb model of angiogenesis. When we used homogenate of mouse hind limb hypoxic tissue instead of bone marrow cell lysate in GST-HIMF pull-down assay; again BTK was shown to bind to GST-HIMF but not to GST (FIG. 1A-1B). These results further indicate that BTK is a HIMF binding partner.

EXAMPLE 3

Co-localization between BTK and HIMF. To demonstrate that BTK acts as a HIMF binding partner in the cells and to better understand the nature of this interaction, we conducted experiments to see if BTK and HIMF co-localize in bone marrow cells. Bone marrow cells were cultured on cover glasses and co-transfected with EGFP-BTK and his-HIMF plasmids. As shown in FIG. 2, BTK and HIMF co-localized in transfected bone marrow cells.

EXAMPLE 4

Translocation of BTK in bone marrow cells in response to the stimulation of HIMF. BTK family tyrosine kinases have been shown to regulate actin cytoskeleton and to mediate cell mobility in response to stimulation (20, 21). The involvement of BTK in thrombin-stimulated platelets (22, 23) indicated that BTK is a mediator of cytoskeleton reorganization. The activation of BTK family tyrosine kinases will result in their stimulated translocation to membrane fractions (24). As a partner of BTK, HIMF may be involved in BTK signaling pathways and play a role in regulation of BTK activity. We therefore conducted an assay to examine whether the distribution of BTK in bone marrow cells was altered in response to stimulation by HIMF. Bone marrow cells were cultured on coverslips in 12 well plates for two days and then treated with HIMF or BSA for 5 minutes at a final concentration of 50 nM. The cells were fixed in pre-cooled methanol at −20° C. for 10 minutes and used for immunocytochemistry.

FIG. 3A-3B show that HIMF rapidly induced recruitment of BTK to the leading edge of cells.

EXAMPLE 5

Figure 5A:
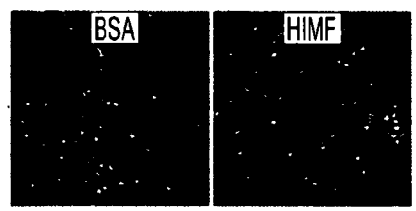
FIGS. 5A-5B. HIMF stimulated bone marrow cell migration. Bone marrow cells were partially digested by trypsin-EDTA solution, washed by PBS and then sucked up and transferred to twelve well plates using a 1000 µl tip. The cells were cultured in 2% fetal bovine serum DMEM with 50 nM BSA or HIMF for four days. More cells migrated out of the original cell colony in the presence of HIMF than those in BSA (FIG. 5A). $5 \times 10^5$ bone marrow cells were cultured in transwell plates in the presence of 50 nM BSA or HIMF. The cells were cultured overnight, fixed in pre-cooled methanol and stained by Coomassie Blue solution. The cells growing on the surface of the membrane were removed after staining (FIG. 5B). A Nikon Eclipse microscope was used for the imaging.
Figure 5B:
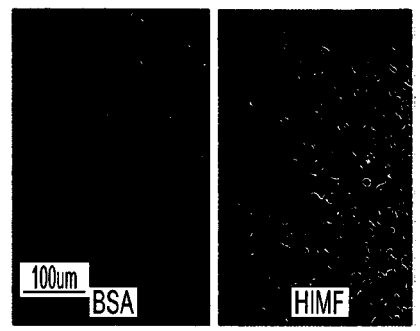

BTK stimulated the migration of bone marrow cells. To test whether HIMF stimulates the migration of bone marrow cells, bone marrow cells were cultured in transwell plates in the presence of 50 µM BSA or HIMF. The cells were cultured overnight, fixed in methanol and stained by Coomassie Blue solution. Cells growing on the surface of the membrane were removed by cotton tipped applicators before imaging. More cells migrated out of the chamber after the treatment of HIMF than the treatment of BSA (FIG. 5A-5B). Cell migration was further determined by partial trypsin digestion culture, leaving the cells to grow in colonies on a cover glass. In the presence of HIMF, more bone marrow cells were stimulated to migrate out of the colony compared to cells treated with bovine serum albumin (BSA) (FIG. 5A-5B).

EXAMPLE 6

Figure 6A:
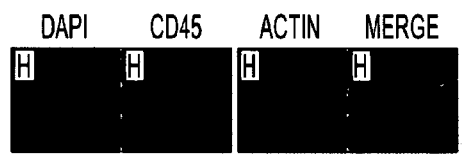
FIGS. 6A-6D. CD45 positive cell migration was stimulated by HIMF and inhibited by BTK inhibitor. Bone marrow cells were cultured on cover glass in 12 well plates as described in FIG. 5A-5B. The cells were then treated with BSA (FIG. 6A) or HIMF (FIG. 6B and FIG. 6C) for 4 days and fixed with pre-cooled methanol before immunocytochemistry with the indicated first antibodies. DAPI staining was used to show the nuclei. The cells migrated out of the original cell colony were shown to be CD45 positive (FIG. 6A, FIG. 6B and FIG. 6C). $5 \times 10^5$ bone marrow cells in 2% fetal bovine serum DMEM culture medium were transferred to each transwell in the presence of 50 nM BSA, HIMF, or HIMF plus 25 µM LFM-A13, respectively. The cells were cultured for 6 hours, fixed in pre-cooled methanol and stained by Coomassie Blue solution. The cells growing on the surface of the membrane were removed after staining. Bone marrow cell migration was induced by HIMF and this induction was inhibited by BTK inhibitor LFM-A13 (FIG. 6D).
Figure 6B:
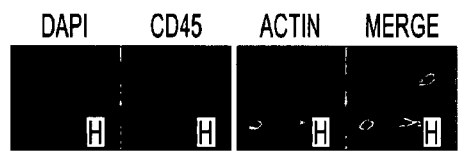
Figure 6C:
Figure 6D:
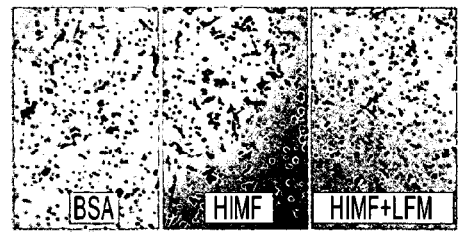

HIMF stimulated CD45 positive cell migration and this migration was blocked by the BTK inhibitor FLM-A13. Since HIMF is an inflammatory factor (3), the upregulation of HIMF may activate an immune response in the hypoxic and inflammatory tissues. We therefore used CD45 antibody to check whether the migrating cells were CD45 positive. As we expected, most of the cells that migrated out of the colony were heavily stained with CD45 antibody (FIG. 6 A, B, and C). To demonstrate whether the BTK signaling pathway is involved in the cell migration induced by HIMF, we conducted an experiment to block the activity of BTK by using LFM-A13, a BTK specific inhibitor, when the cells were treated with HIMF. As shown in FIG. 6D, BTK inhibitor LFM-A13 completely blocked the cell migration induced by BTK.

EXAMPLE 7

HIMF promoted angiogenesis in hypoxic tissues. Hypoxia can induce pulmonary artery adventitial remodeling and neovascularization. The progenitor cells derived from bone marrow may contribute to postnatal neovascularization and vascular wall thickening as occurs with development of pulmonary hypertension (25). Since HIMF can activate bone marrow cells and induce the auto-phosphorylation of BTK and stimulate the migration of CD 45 positive cells, HIMF may have a function in recruiting leukocytes and progenitor cells to the hypoxic tissues. To further examine whether HIMF recruits EPCs to the hypoxic tissues, BSA or HIMF was mixed with 2% agarose at a final concentration of 100 nM, gelled on ice and implanted to the sites of hypoxic tissues in mouse hindlimb ischemia model. Two weeks after implantation, the tissues were collected for sectioning and immunostaining. As shown by EPC marker molecule CD34 (FIG. 7A-7B), HIMF stimulated angiogenesis in hindlimb ischemia tissues. CD34 positive cells were increased in the tissue treated with HIMF compared to the tissue treated with control BSA containing gel.

EXAMPLE 8

Figure 8:
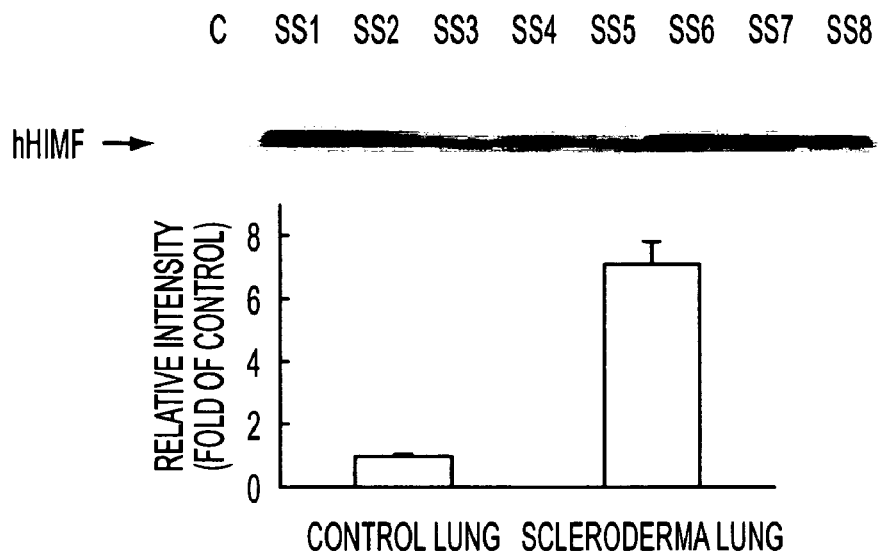
FIG. 8. Human HIMF up-regulated in scleroderma patient lungs relative to control lungs. The HIMF proteins were measured immunohistochemically and quantitated.

HIMF isoforms RELMα and RELMβ, are upregulated in lungs from scleroderma and IPAH patients. Human HIMF isoforms were measured immunochemically in control and scleroderma lung. Results are shown in FIG. 8. A greater than six-fold increase was observed.

EXAMPLE 9

Genomic studies performed from peripheral blood in patients with idiopathic pulmonary hypertension demonstrate an increase in resistin expression.

TABLE 1

Genes showing significant changes ($P < 0.05$ or $Q < 1\%$ in expression in PBMCs of IPAH patients

| Fold increase in IPAH patients | Fold-increase in PAH/SS patients | Description |
|---|---|---|
| 5.60 | 6.16 | Vascular endothelial growth factor |
| 2.84 | NS | Resistin |
| 2.22 | 4.87 | Pre-B-cell colony enhancing factor 1 |
| NS | 2.89 | Matrix metalloproteinase 9 9gelatinase B, 92 kD Type IV collagena |
| 1.72 | 1.74 | Granzyme B (cytotoxic T lymphocyte-associated serine esterase 1) |

EXAMPLE 10

Treatment of hypoxic rats with simvastatin also blocks hypoxia-induced expression of HIMF within the lung.

Figure 9:
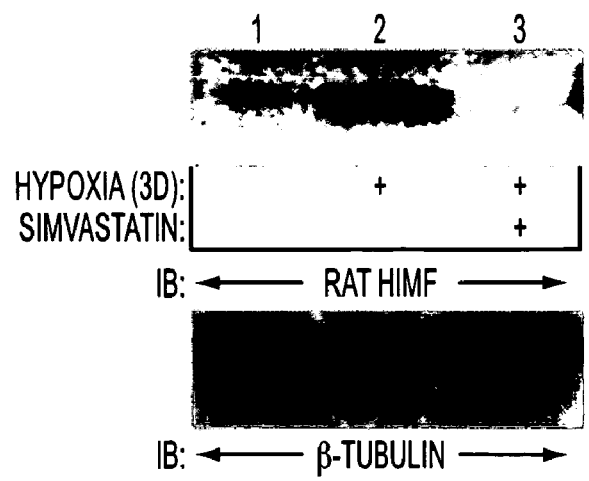
FIG. 9. Expression of HIMF and beta-tubulin under hypoxic conditions and/or with statin treatment. Immunoblots of HIMF (top) and beta-tubulin (bottom) with conditions as indicated.

Adult male Sprague-Dawley rats were exposed (14 d) to normoxia (N), normoxia plus once daily simvastatin (20 mg/kg IP) (NS), hypoxia (10% FiO2) (H) or hypoxia plus simvastatin (HS). Western blot analysis revealed almost complete reduction of HIMF expression in the lungs of simvastatin treated rats exposed to hypoxia. See FIG. 9. Beta-tubulin expression was measured as a control and did not vary under these conditions.

The disclosure of each reference cited is expressly incorporated herein.

REFERENCES

1. Teng X, Li D, Champion H C, Johns R A. FIZZ1/RELMalpha, a novel hypoxia-induced mitogenic factor in lung with vasoconstrictive and angiogenic properties. *Circ Res.* 2003; 92(10):1065-7.
2. Wagner K F, Hellberg A K, Balenger S, Depping R, Dodd-O J, Johns R A, Li D. Hypoxia induced mitogenic factor has antiapoptotic action and is upregulated in the developing lung: coexpression with hypoxia-inducible factor-2alpha. *Am J Respir Cell Mol. Biol.* 2004; 31 (3): 276-282.
3. Holcomb I N, Kabakoff R C, Chan B, Baker T W, Gurney A, Henzel W, Nelson C, Lowman H B, Wright B D, Skelton N J, Frantz G D, Tumas D B, Peale Jr F V, Shelton D L, Hebert C C. FIZZ1, a novel cysteine-rich secreted protein associated with pulmonary inflammation, defines a new gene family. *EMBO J.* 2000; 19(15):4046-4055.
4. Nair M G, Gallagher I J, Taylor M D, Loke P, Coulson P S, Wilson R A, Maizels R M, Allen J E. Chitinase and Fizz family members are a generalized feature of Nematode infection with selective upregulation of Ym1 and Fizz1 by antigen presenting cells. *Infect Immun.* 2005; 73(1):385-394.
5. Burnett M S, Lee C W, Kinnaird T D, Stabile E, Durrani S, Dullum M K, Devaney J M, Fishman C, Stamou S, Canos D, Zbinden S, Clavijo L C, Jang G J, Andrews J A, Zhu J, Epstein S E. The potential role of resistin in atherogenesis. *Atherosclerosis.* 2005; 182(2):241-8.
6. Wolf G. Insulin resistance and obesity: resistin, a hormone secreted by adipose tissue. *Nutr Rev.* 2004; 62(10):389-94.
7. Chumakov A. M., T. Kubota, S. Walter, H. P. Koeffler. Identification of murine and human XCP1 genes as C/EBP-epsilon-dependent members of FIZZ/Resistin gene family. *Oncogene.* 2004; 23(19):3414-3425.

8. Tepper O M, Capla J M, Galiano R D, Ceradini D J, Callaghan M J, Kleinman M E, Gurtner G C. Adult vasculogenesis occurs through in situ recruitment, proliferation, and tubulization of circulating bone marrow-derived cells. *Blood.* 2005; 105(3):1068-1077.
9. Grant M B, May W S, Caballero S, Brown G A, Guthrie S M, Mames R N, Byrne B J, Vaught T, Spoerri P E, Peck A B, Scott E W. Adult hematopoietic stem cells provide functional hemangioblast activity during retinal neovascularization. *Nat. Med.* 2002; 8: 607-612.
10. Zhang Z G, Zhang L, Jiang Q, and Chopp M. Bone marrow-derived endothelial progenitor cells participate in cerebral neovascularization after focal cerebral ischemia in the adult mouse. *Circ Res.* 2002; 90:284-288.
11. Asahara T, Masuda H, Takahashi T, Kalka C, Pastore C, Silver M, Keame M, Magner M, Isner J M. Bone marrow origin of endothelial progenitor cells responsible for postnatal vasculogenesis in physiological and pathological neovascularization. *Circ Res.* 1999; 85:221-228.
12. Lin Y, Weisdorf D J, Solovey A, Hebbel H R. Origins of circulating endothelial cells and endothelial outgrowth from blood. *J Clin Invest.* 2000; 105(1):71-77.
13. Henrich D, Hahn P, Wahl M, Wilhelm K, Dernbach E, Dimmeler S, and Marzi I. Serum derived from multiple trauma patients promotes the differentiation of endothelial progenitor cells in vitro: possible role of transforming growth factor-beta1 and vascular endothelial growth factor 165. *Shock.* 2004; 21(1):13-16.
14. Scapini P, Morini M, Tecchio C, Minghelli S, Di Carlo E, Tanghetti E, Albini A, Lowell C, Berton G, Noonan D M, Cassatella M A. CXCL1/macrophage Inflammatory protein-2-induced angiogenesis in vivo is mediated by neutrophil-derived vascular endothelial growth actor-A. *J Immunol.* 2004; 172(8):5034-5040.
15. Khakoo A Y, and Finkel T. Endothelial progenitor cells. *Annu Rev Med.* 2005; 56:79-101.
16. Takahashi T, Kalka C, Masuda H, Chen D, Silver M, Kearney M, Magner M, Isner J M, Asahara T. Ischemia- and cytokine-induced mobilization of bone marrow-derived endothelial progenitor cells for neovascularization. *Nat. Med.* 1999; 5(4):434-438.
17. Reyes M, Dudek A, Jahagirdar B, Koodie L, Marker P H, Verfaillie C M. Origin of endothelial progenitors in human postnatal bone marrow. *J Clin Invest.* 2002; 109(3):337-46.
18. Vetrie D, Vorechovsky I, Sideras P, Holland J, Davies A, Flinter F, Hammarstorm L, Kinnon C, Levinsky R, Bobrow M, Smith C I E, Bentley D R. The gene involved in X-linked agammaglobulinaemia is a member of the src family of protein-tyrosine kinases. *Nature.* 1993; 361(6409):226-233.
19. Thomas J D, Sideras P, Smith C I, Vorechovsky I, Chapman V, Paul W E. Colocalization of X-linked agammaglobulinemia and X-linked immunodeficiency genes. *Science.* 1993; 261(5119):355-358.
20. Mangla A, Khare A, Vineeth V, Panday N N, Mukhopadhyay A, Ravindran B, Bal V, George A, and Rath S. Pleiotropic consequences of Bruton tyrosine kinase deficiency in myeloid lineages lead to poor inflammatory responses. *Blood.* 2004; 104(4):1191-1197.
21. Abassi Y A, Rehn M, Ekman N, Alitalo K, Vuori K. p130Cas couples the tyrosine kinase Bmx/Etk with regulation of the actin cytoskeleton and cell migration. *J Biol. Chem.* 2003; 278(37):35636-35643.
22. Laffargue M, Ragab-Thomas J M, Ragab A, Tuech J, Missy K, Monnereau L, Blank U, Plantavid M, Payrastre B, Raynal P, Chap H. Phosphoinositide 3-kinase and integrin signalling are involved in activation of Bruton tyrosine kinase in thrombin-stimulated platelets. *FEBS Lett.* 1999; 443(1):66-70.
23. Hamazaki Y, Kojima H, Mano H, Nagata Y, Todokoro K, Abe T, Nagasawa T. Tec is involved in G protein-coupled receptor- and integrin-mediated signalings in human blood platelets. *Oncogene.* 1998; 16(21):2773-2779.
24. Varnai P, Rother K I, Balla T. Phosphatidylinositol 3-kinase-dependent membrane association of the Bruton's tyrosine kinase pleckstrin homology domain visualized in single living cells. *J Biol. Chem.* 1999; 274(16):10983-10989.
25. Davie N J, Crossno Jr J T, Frid M G, Hofmeister S E, J. Reeves T, Hyde D M, Carpenter C T, Brunetti J A, McNiece I K, Stenmark K R. Hypoxia-induced pulmonary artery adventitial remodeling and neovascularization: contribution of progenitor cells. *Am J Physiol Lung Cell Mol. Physiol.* 2004; 286(4):L668-L678.
26. Steppan C M, Bailey S T, Bhat S, Brown E J, Banerjee R R, Wright C M, Patel H R, Ahima R S, Lazar M A. The hormone resistin links obesity to diabetes. *Nature.* 2001; 18(409):307-12.
27. Burnett M S, Lee C W, Kinnaird T D, Stabile E, Durrani S, Dullum M K, Devaney J M, Fishman C, Stamou S, Canos D, Zbinden S, Clavijo L C, Jang G J, Andrews J A, Zhu J, Epstein S E. The potential role of resistin in atherogenesis. *Atherosclerosis.* 2005; 182(2):241-8.
28. Yang W, Desiderio S. BAP-135, a target for Bruton's tyrosine kinase in response to B cell receptor engagement. *Proc Natl Acad Sci USA.* 1997; 94(2):604-609.
29. Ghosh S, May M J, Kopp E B. NF-kappa B and Rel proteins: evolutionarily conserved mediators of immune responses. *Annu Rev Immunol.* 1998; 16:225-260.
30. Jackson T. A., Taylor H E, Sharma D, Desiderio S, Danoff S K. Vascular Endothelial Growth Factor Receptor-2: counter-regulation by the transcription factors, TFII-I and TFII-IRD1. *J Biol. Chem.* 2005; 280(33):29856-29863.
31. Jefferies C A and O'Neill L A. Bruton's tyrosine kinase (Btk)—the critical tyrosine kinase in LPS signalling? *Immunol Lett.* 2004; 92(1-2):15-22.
32. Chen R, Kim O, Li M, Xiong X, J. Guan L, Kung H J, Chen H, Shimizu Y, Qiu Y. Regulation of the PH-domain-containing tyrosine kinase Etk by focal adhesion kinase through the FERM domain. *Nat Cell Biol.* 2001; 3(5):439-444.
33. Chavakis E, Aicher A, Heeschen C, Sasaki K, Kaiser R, El Makhfi N, Urbich C, Peters T, Scharffetter-Kochanek K, Zeiher A M, Chavakis T, Dimmeler S. Role of beta2-integrins for homing and neovascularization capacity of endothelial progenitor cells. *J Exp Med.* 2005; 201(1):63-72.

The invention claimed is:

1. A method of treating a patient with Emphysema comprising:
   administering to the patient an antibody which specifically binds to HIMF (SEQ ID NO:1 or 2);
   whereby binding of HIMF to BTK is inhibited.

* * * * *

SEQUENCE LISTING

<160> NUMBER OF SEQ ID NOS: 6

<210> SEQ ID NO 1
<211> LENGTH: 108

```
<212> TYPE: PRT
<213> ORGANISM: Homo sapiens

<400> SEQUENCE: 1

Met Lys Ala Leu Cys Leu Leu Leu Pro Val Gly Leu Leu Val
 1               5                  10                  15

Ser Ser Lys Thr Leu Cys Ser Met Glu Glu Ala Ile Asn Glu Arg Ile
            20                  25                  30

Gln Glu Val Ala Gly Ser Leu Ile Phe Arg Ala Ile Ser Ile Gly
            35                  40                  45

Leu Glu Cys Gln Ser Val Thr Ser Arg Gly Asp Leu Ala Thr Cys Pro
 50                      55                  60

Arg Gly Phe Ala Val Thr Gly Cys Thr Cys Gly Ser Ala Cys Gly Ser
65              70                  75                  80

Trp Asp Val Arg Ala Glu Thr Thr Cys His Cys Gln Cys Ala Gly Met
                85                  90                      95

Asp Trp Thr Gly Ala Arg Cys Cys Arg Val Gln Pro
                100                 105

<210> SEQ ID NO 2
<211> LENGTH: 111
<212> TYPE: PRT
<213> ORGANISM: Homo sapiens

<400> SEQUENCE: 2

Met Gly Pro Ser Ser Cys Leu Leu Ile Leu Ile Pro Leu Leu Gln
 1               5                  10                  15

Leu Ile Asn Pro Gly Ser Thr Gln Cys Ser Leu Asp Ser Val Met Asp
            20                  25                  30

Lys Lys Ile Lys Asp Val Leu Asn Ser Leu Glu Tyr Ser Pro Ser Pro
            35                  40                  45

Ile Ser Lys Lys Leu Ser Cys Ala Ser Val Lys Ser Gln Gly Arg Pro
 50                      55                  60

Ser Ser Cys Pro Ala Gly Met Ala Val Thr Gly Cys Ala Cys Gly Tyr
65              70                  75                  80

Gly Cys Gly Ser Trp Asp Val Gln Leu Glu Thr Thr Cys His Cys Gln
                85                  90                      95

Cys Ser Val Val Asp Trp Thr Thr Ala Arg Cys Cys His Leu Thr
                100                 105                 110

<210> SEQ ID NO 3
<211> LENGTH: 659
<212> TYPE: PRT
<213> ORGANISM: Homo sapiens

<400> SEQUENCE: 3

Met Ala Ala Val Ile Leu Glu Ser Ile Phe Leu Lys Arg Ser Gln Gln
 1               5                  10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
            35                  40                  45

Arg Gly Ser Lys Lys Gly Ser Ile Asp Val Glu Lys Ile Thr Cys Val
 50                      55                  60

Glu Thr Val Val Pro Glu Lys Asn Pro Pro Glu Arg Gln Ile Pro
65              70                      75                  80

Arg Arg Gly Glu Glu Ser Ser Glu Met Glu Gln Ile Ser Ile Ile Glu
                85                  90                      95
```

```
Arg Phe Pro Tyr Pro Phe Gln Val Val Tyr Asp Glu Gly Pro Leu Tyr
                100                 105                 110

Val Phe Ser Pro Thr Glu Glu Leu Arg Lys Arg Trp Ile His Gln Leu
            115                 120                 125

Lys Asn Val Ile Arg Tyr Asn Ser Asp Leu Val Gln Lys Tyr His Pro
        130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
        355                 360                 365

Leu Ile Ser Arg Leu Lys Tyr Pro Val Ser Gln Asn Lys Asn Ala
370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
            420                 425                 430

Lys Glu Gly Ser Met Ser Glu Asp Glu Phe Ile Glu Glu Ala Lys Val
        435                 440                 445

Met Met Asn Leu Ser His Glu Lys Leu Val Gln Leu Tyr Gly Val Cys
450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
```

515                 520                 525
Val Asn Asp Gln Gly Val Val Lys Val Ser Asp Phe Gly Leu Ser Arg
    530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
            580                 585                 590

Leu Gly Lys Met Pro Tyr Glu Arg Phe Thr Asn Ser Glu Thr Ala Glu
        595                 600                 605

His Ile Ala Gln Gly Leu Arg Leu Tyr Arg Pro His Leu Ala Ser Glu
    610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
                645                 650                 655

Glu Glu Ser

<210> SEQ ID NO 4
<211> LENGTH: 470
<212> TYPE: DNA
<213> ORGANISM: Homo sapiens

<400> SEQUENCE: 4
gtgtgccgga tttggttagc tgagcccacc gagagggatg aaagctctct gtctcctcct      60
cctccctgtc ctggggctgt tggtgtctag caagaccctg tgctccatgg aagaagccat     120
caatgagagg atccaggagg tcgccggctc cctaatattt agggcaataa gcagcattgg     180
cctggagtgc cagagcgtca cctccagggg ggacctggct acttgccccc gaggcttcgc     240
cgtcaccggc tgcacttgtg gctccgcctg tggctcgtgg gatgtgcgcg ccgagaccac     300
atgtcactgc cagtgcgcgg gcatggactg gaccggagcg cgctgctgtc gtgtgcagcc     360
ctgaggtcgc gcgcagcgcg tgcacagcgc gggcggaggc ggctccaggt ccggaggggt     420
tgcgggggag ctggaaataa acctggagat gatgatgatg atgatgatgg                 470

<210> SEQ ID NO 5
<211> LENGTH: 595
<212> TYPE: DNA
<213> ORGANISM: Homo sapiens

<400> SEQUENCE: 5
gccacgttgt cttctttcct tcaccaccac ccaggagctc agagatctaa gctgctttcc      60 atctttctc ccagccccag gacactgact ctgtacagga tggggccgtc ctcttgcctc     120
cttctcatcc taatccccct tctccagctg atcaacccgg ggagtactca gtgttcctta     180
gactccgtta tggataagaa gatcaaggat gttctcaaca gtctagagta cagtccctct     240
cctataagca agaagctctc gtgtgctagt gtcaaaagcc aaggcagacc gtcctcctgc     300
cctgctggga tggctgtcac tggctgtgct tgtggctatg ctgtggttc gtgggatgtt     360 cagctggaaa ccacctgcca ctgccagtgc agtgtggtgg actggaccac tgcccgctgc     420
tgccacctga cctgacaggg aggaggctga gaactcagtt ttgtgaccat gacagtaatg     480
aaaccagggt cccaaccaag aaatctaact caaacgtccc acttcatttg ttccattcct     540
gattcttggg taataaagac aaactttgta cctcaaaaaa aaaaaaaaaa aaaaa           595

<210> SEQ ID NO 6
<211> LENGTH: 2591
<212> TYPE: DNA
<213> ORGANISM: Homo sapiens

<400> SEQUENCE: 6

| | | | | | |
|---|---|---|---|---|---|
| ctcagactgt | ccttcctctc | tggactgtaa | gaatatgtct | ccagggccag | tgtctgctgc | 60 |
| gatcgagtcc | caccttccaa | gtcctggcat | ctcaatgcat | ctgggaagct | acctgcatta | 120 |
| agtcaggact | gagcacacag | gtgaactcca | gaaagaagaa | gctatggccg | cagtgattct | 180 |
| ggagagcatc | tttctgaagc | gatcccaaca | gaaaaagaaa | acatcacctc | taaacttcaa | 240 |
| gaagcgcctg | tttctcttga | ccgtgcacaa | actctcctac | tatgagtatg | actttgaacg | 300 |
| tgggagaaga | ggcagtaaga | agggttcaat | agatgttgag | aagatcactt | gtgttgaaac | 360 |
| agtggttcct | gaaaaaaatc | ctcctccaga | aagacagatt | ccgagaagag | gtgaagagtc | 420 |
| cagtgaaatg | gagcaaattt | caatcattga | aaggttccct | tatcccttcc | aggttgtata | 480 |
| tgatgaaggg | cctctctacg | tcttctcccc | aactgaagaa | ctaaggaagc | ggtggattca | 540 |
| ccagctcaaa | aacgtaatcc | ggtacaacag | tgatctggtt | cagaaatatc | acccttgctt | 600 |
| ctggatcgat | gggcagtatc | tctgctgctc | tcagacagcc | aaaaatgcta | tgggctgcca | 660 |
| aattttggag | aacaggaatg | gaagcttaaa | acctgggagt | tctcaccgga | agacaaaaaa | 720 |
| gcctcttccc | ccaacgcctg | aggaggacca | gatcttgaaa | aagccactac | cgcctgagcc | 780 |
| agcagcagca | ccagtctcca | caagtgagct | gaaaaaggtt | gtggccccttt | atgattacat | 840 |
| gccaatgaat | gcaaatgatc | tacagctgcg | aaggggtgat | gaatatttta | tcttggagga | 900 |
| aagcaactta | ccatggtgga | gagcacgaga | taaaaatggg | caggaaggct | acattcctag | 960 |
| taactatgtc | actgaagcag | aagactccat | agaaatgtat | gagtggtatt | ccaaacacat | 1020 |
| gactcggagt | caggctgagc | aactgctaaa | gcaagagggg | aaagaaggag | gtttcattgt | 1080 |
| cagagactcc | agcaaagctg | gcaaatatac | agtgtctgtg | tttgctaaat | ccacagggga | 1140 |
| ccctcaaggg | gtgatacgtc | attatgttgt | gtgttccaca | cctcagagcc | agtattacct | 1200 |
| ggctgagaag | cacttttca | gcaccatccc | tgagctcatt | aactaccatc | agcacaactc | 1260 |
| tgcaggactc | atatccaggc | tcaaatatcc | agtgtctcaa | caaaacaaga | atgcaccttc | 1320 |
| cactgcaggc | ctgggatacg | gatcatggga | aattgatcca | aaggacctga | ccttcttgaa | 1380 |
| ggagctgggg | actggacaat | tggggtagt | gaagtatggg | aaatggagag | gccagtacga | 1440 |
| cgtggccatc | aagatgatca | agaaggctc | catgtctgaa | gatgaattca | ttgaagaagc | 1500 |
| caaagtcatg | atgaatcttt | cccatgagaa | gctggtgcag | ttgtatggcg | tctgcaccaa | 1560 |
| gcagcgcccc | atcttcatca | tcactgagta | catggccaat | ggctgcctcc | tgaactacct | 1620 |
| gagggagatg | cgccaccgct | tccagactca | gcagctgcta | gagatgtgca | aggatgtctg | 1680 |
| tgaagccatg | gaatacctgg | agtcaaagca | gttccttcac | cgagacctgg | cagctcgaaa | 1740 |
| ctgtttggta | aacgatcaag | gagttgttaa | agtatctgat | ttcggcctgt | ccaggtatgt | 1800 |
| cctggatgat | gaatacacaa | gctcagtagg | ctccaaattt | ccagtccggt | ggtccccacc | 1860 |
| ggaagtcctg | atgtatagca | agttcagcag | caaatctgac | atttgggctt | tgggggtttt | 1920 |
| gatgtgggaa | atttactccc | tggggaagat | gccatatgag | agatttacta | acagtgagac | 1980 |
| tgctgaacac | attgcccaag | gcctacgtct | ctacaggcct | catctggctt | cagagaaggt | 2040 |
| atataccatc | atgtacagtt | gttggcatga | gaaagcagat | gagcgtccca | ctttcaaaat | 2100 |
| tcttctgagc | aatattctag | atgtcatgga | tgaagaatcc | tgagctcgcc | aataagcttc | 2160 |

| | |
|---|---|
| ttggttctac ttctcttctc cacaagcccc aatttcactt tctcagagga aatcccaagc | 2220 |
| ttaggagccc tggagccttt gtgctcccac tcaatacaaa aaggccctc tctacatctg | 2280 |
| gggatgcacc tcttctttga ttccctggga tagtggcttc tgagcaaagg ccaaaaaatt | 2340 |
| attgtgcctg aaatttcccg agagaattaa gacagactga atttgcgatg aaaatatttt | 2400 |
| ttaggaggga ggatgtaaat agccgcacaa aggggtccaa cagctctttg agtaggcatt | 2460 |
| tggtagagct tgggggtgtg tgtgtggggg tggaccgaat ttggcaagaa tgaaatggtg | 2520 |
| tcataaagat gggaggggag ggtgttttga taaaataaat tctagaaagc ttaaaaaaaa | 2580 |
| aaaaaaaaaa a | 2591 |